United States Patent [19]

Anderson

[11] Patent Number: 4,900,446

[45] Date of Patent: Feb. 13, 1990

[54] CENTRIFUGAL FAST CHROMATOGRAPH

[75] Inventor: Norman G. Anderson, Rockville, Md.

[73] Assignee: Large Scale Biology, Rockville, Md.

[21] Appl. No.: 331,357

[22] Filed: Mar. 31, 1989

Related U.S. Application Data

[60] Division of Ser. No. 210,160, Jun. 9, 1988, abandoned, which is a continuation of Ser. No. 65,590, Jun. 23, 1987, abandoned.

[51] Int. Cl.$^4$ .............................................. B01D 15/08
[52] U.S. Cl. ................................... 210/657; 210/96.1; 210/198.2; 210/745; 73/61.1 C; 422/70; 436/161
[58] Field of Search ..................... 210/96.1, 198.2, 657, 210/745; 422/70; 73/61.1 C; 436/161

[56] References Cited

U.S. PATENT DOCUMENTS

| | | | |
|---|---|---|---|
| 3,113,103 | 12/1963 | Lowery | 210/657 |
| 3,547,547 | 12/1970 | Anderson | 356/197 |
| 3,555,284 | 1/1970 | Anderson | 250/356 |
| 3,582,218 | 6/1971 | Anderson | 356/356 |
| 3,617,557 | 11/1971 | Giltrow | 210/198.2 |
| 3,798,459 | 3/1974 | Anderson et al. | 250/250 |
| 3,813,031 | 5/1974 | Anderson | 233/26 |
| 4,422,941 | 12/1983 | Vaughan, Jr. et al. | 210/210 |
| 4,545,904 | 10/1985 | Tehrani | 210/198.2 |
| 4,595,495 | 6/1986 | Yotam et al. | 210/210 |
| 4,595,496 | 6/1986 | Carson | 210/210 |
| 4,632,762 | 12/1986 | Ramsland | 210/657 |
| 4,678,570 | 7/1987 | Meszaros et al. | 210/198.2 |

OTHER PUBLICATIONS

Chemical Abstracts, vol. 73, 1970, p. 83677, #83635s.
Chemical Abstracts, vol. 74, 1971, p. 51, #649w.
Bock, R. M. and Ling, N.S., *Anal. Chem.*, 26: (1954), pp. 1543–1546.
Anderson, "Analytical Techniques for Cell Fractions. I. Simplified Gradient Programming", *Anal. Biochem.*, 3: pp. 472–478, (1962).
Anderson, "Analytical Techniques for Cell Fractions. VII. A Simple Gradient-Forming Apparatus", *Anal. Biochem.*, 21: 259–265, 1967.
Albright, A Method for Rapid Fractionation of Particulate Systems by Gradient Differential Centrifugation, Exptl. Cell Res., 15: pp. 271–281, (1958).
Candler, Analytical Techniques for Cell Fractions. VI. Multiple Gradient-Distribution Rotor (B-XXI), Anal. Biochem., 21: 253–258, 1967.
Scott, Dynamic Introduction of Whole Blood Samples, Clin. Chem., 18: 749–752, 1972.
Bartis, Optimization and Analytical Applications of the Technique of dynamic Introduction of Liquids into Centrifugal Analyzers, Clin. Chem., 20: 932–41, (1974).
Anderson, Analytical Techniques for Cell Fractions. XII. A Multiple-Cuvet Rotor for a New Microanalytical System, Anal. Biochem., 28: 545–562, (1969).
Anderson, Computer–Interfaced Fast Analyzers, Science, 166: 317–324, 1969.
Anderson, The Development of Fast Analyzers, N.G., Z. Anal. Chem., 261: 257–271, (1972).
Maclin, A System Analysis of GeMSAEC Precision in Used as a Kinetic Enzyme Analyzer, Clin. Chem., 17: 707–714, (1971).
Maclin, Relationship Between Variable in Instrument Performance and Results of Kinetic Enzyme Assays, Clin. Chem., 19: 832–837, (1973).
Anderson, Analytical Techniques for Cell Fractions, XIV, Use of Drainage Syphons in a Fast–Analyzer Cuvet-Rotor, Anal. Bichem., 32: 59–69, (1969).
Scott, Centrifugal Elution Chromatography with Eluate Monitoring, Chromatogr., 99: 35–42, (1974).

(List continued on next page.)

Primary Examiner—Ernest G. Therkorn
Attorney, Agent, or Firm—Robbins & Laramie

[57] ABSTRACT

A centrifugal fast chromatograph is disclosed. The apparatus includes a rotor, a rotor drive, a plurality of chromatographic columns mounted on the rotor, a transfer disk mounted on the rotor, photodetecting apparatus, a gradient maker and a microprocessor control system. The microprocessor controls and monitors the entire chromatography process. The centrifugal fast chromatograph permits the performance of multiple, rapid, and simultaneous separations.

11 Claims, 9 Drawing Sheets

OTHER PUBLICATIONS

Shimate, Centrifugal System for Affinity Chromatography with Eluate Monitoring, Clin. Chem., 22: 1493–6, (1976).

Anderson, An Introduction to Particle Separation in Zonal Centrifuges, Natl. Cancer Inst. Monogr., 21: 9–39, (1966).

Pitt, Simultaneous Multicolumn Operation of the UV Analyzer for Body Fluids, Clinical Chem., 18: 767–770, (1972).

Ertingshausen, Adaptation of a T3–Uptake Test and of Radioimmunoassays for Serum Digoxin, Thyroxine, and Triiodothyronine to an Automated Readioimmunoassay System—"Centria", Clin. Chem., 21: 1305–1313.

Herndon, Horizontal Chromatography Accelerating Apparatus, Description and Applications, Anal. Chem., 34: 1061–1064, (1962), 13.

Matthews, Steroids, CCXI, Centrifugally Accelerated Paper Partition Chromatography of Steroids, Chromatograph., 9: 195–198, (1962).

Ribi, Chromatography of Microbial Lipids by Centrifugation Through Microparticulate Gel, Bacteriol., 102: 250–260, (1970).

Marihuana: Identification of Cannabanoids by Centrifugal Chromatography, Science, 173: 824–826, 1971.

Anacker, Separation of Sugars by Centrifugal Microparticulate Bed Chromatography, Chromatogr., 62: 93–97, 1971.

Ribi, Pressure–Accelerated Chromatography Through Microparticulate Silica Columns Packed by Centrifugation, Chromatogr. Sci., 10: 708–711, 1972.

Rosates, Evaluation of Centrifugal Chromatography, I, Separation of Steroid Hormones on Silica Gel, Chromatogr. Sci., 11: 406–410, 1973.

Wyszynski, Centrifugal Chromatography of Free and Dansylated Amino Acids, Chromatography, 115: 665–669, (1975).

Ito, Counter–Current Chromatography Through the Coil–Planet Centrifuge, Science, 173: (1971), pp. 420–422.

Ito, The Elution Centrifuge Applied to Countercurrent Chromatography, Anal. Biochem., 49: 1–8, 1972.

Atherton, Chromatography and Zonal Centrifugation, Anal. Biochem., 49: (1972), pp. 326–335.

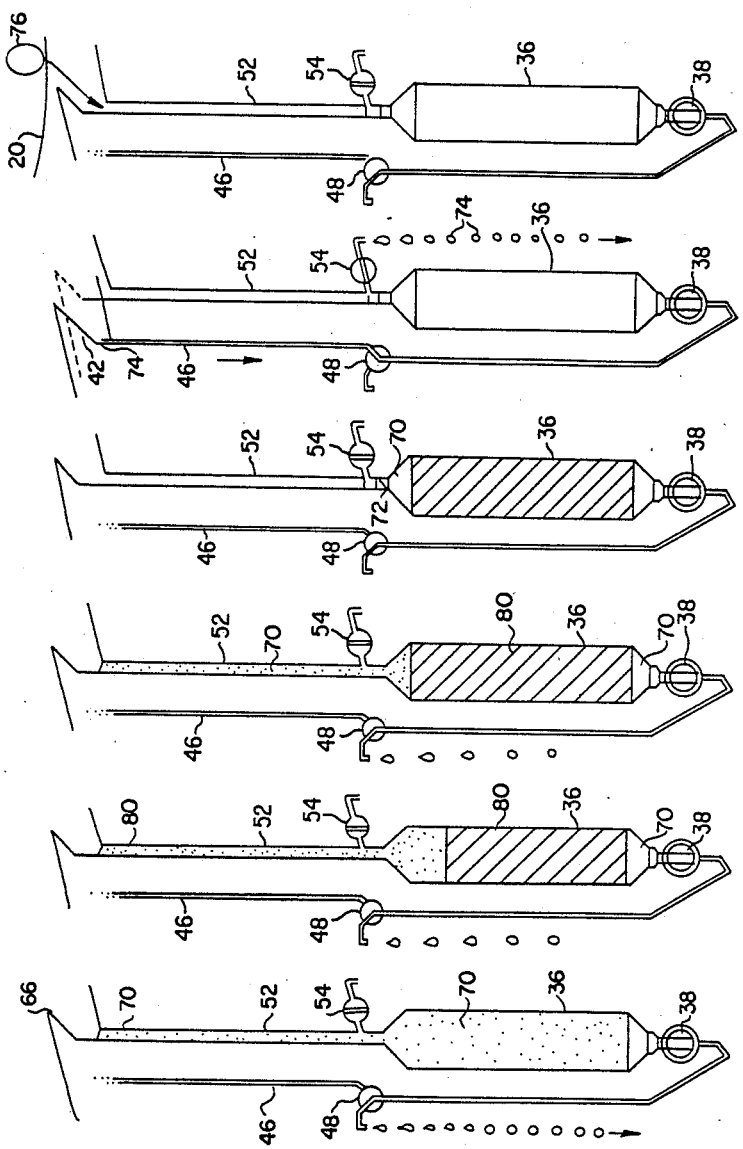

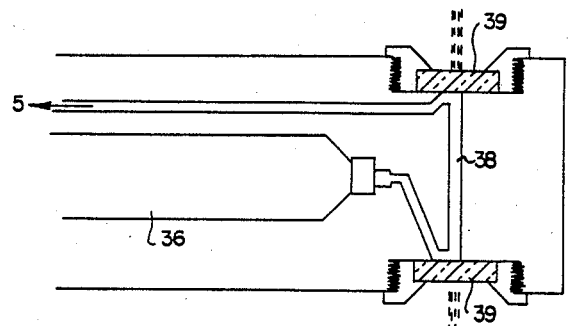
FIG. 6A
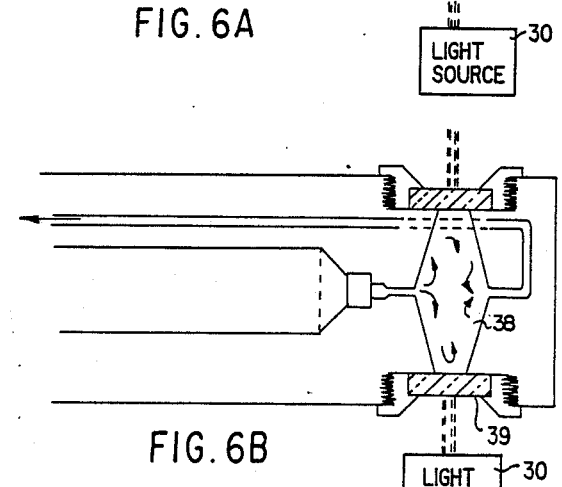
FIG. 6B
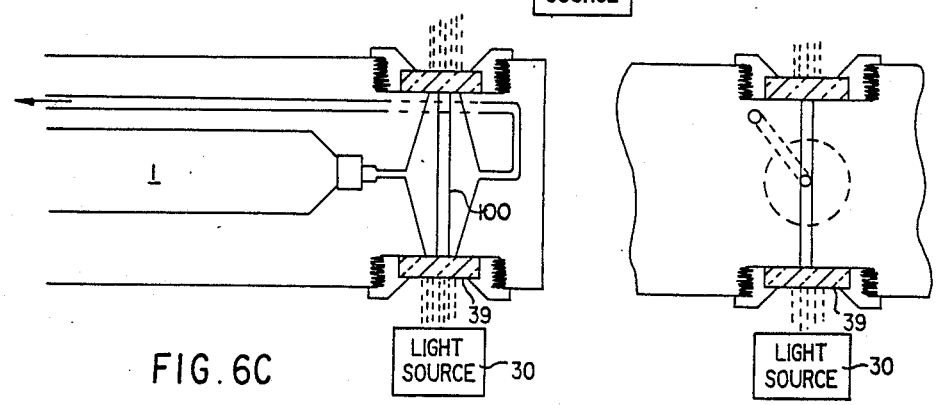
FIG. 6C
FIG. 6D

CENTRIFUGAL FAST CHROMATOGRAPH

This is a division of application Ser. No. 210,160, filed June 9, 1988, now abandoned, which is a continuation of Ser. No. 065,590, filed Jun. 23, 1987, now abandoned.

TECHNICAL FIELD

The present invention relates to an improved centrifugal chromatograph. In particular, the present invention relates to a centrifugal chromatograph wherein multiple separations may be performed simultaneously, rapidly, and relatively inexpensively.

BACKGROUND OF THE INVENTION

High-pressure, high-resolution liquid chromatography has come into wide use to separate proteins, nucleic acids, metabolites, drugs, and a wide variety of compounds both in the research laboratory, in industry, and in clinical laboratories. The systems now in use are expensive, and include non-pulsating high-pressure pumps, valving (often operating at high pressure) for sample introduction, high-pressure prepacked columns, small uniform beads adapted to achieve high resolution separations, a spectrophotometer or colorimeter to monitor each column, and a fraction collector for each column as essential components. In addition, microprocessor systems for analysis of the chromatographs, programs to integrate peaks, and a printer to print out quantitative results are also used. The systems do not include positive means to prevent anomalous flow or channelling to insure ideal flow through the column, to positively remove air bubbles, to prevent a column from running dry during use, to prevent anomalous flow and mixing either in the headspace above the column where flow fans out from the narrow-bore inlet tubing to the full bore of the separations column, or where the converse restriction in diameter occurs as liquid leaves the column and is constricted into the detector flow cell. In addition, the rapid data processing capabilities of microprocessors are not fully used; although one microprocessor can now process, manage, and display data from a dozen or more columns, microprocessors are not so used.

In presently available systems the entire collection of components service, drive, and monitor only one column at a time, can perform only one analysis at a time, is expensive, is subject to a variety of operational problems which may produce anomalous results, and procedures resolution lower than that which should, theoretically, be obtained. Additionally, packing new columns or repacking with cleaned column separation materials is difficult if not impossible in the field.

One recent development has altered the instrumental requirements for high resolution separations. This is the development of very uniform spherical beads or resins which reduce the back pressure required to achieve high resolution. Where thousands of pounds per square inch of pressure have been required previously, only hundreds are required now. This means that the pressure requirements can be met in a centrifugal field at much lower speeds. The mechanical strength of the beads has also increased to prevent their deformation under pressure. This higher strength also produces resistance to deformation in centrifugal fields.

Prior noncentrifugal chromatographs encountered numerous other problems. There was no automatic compensation for flow resistance in different columns. When a number of parallel columns are fed from one pump to a non-centrifugal system, the flow through different columns will be slightly different depending on differences in flow resistance in individual columns.

In column chromatography there has not previously been a method for preventing anomalous flow such as channeling through the packing. If the packing is uneven, or if the packing particles are of different sizes, the resistance to flow in different parts of the column will be different. Liquid will flow through the lines or channels of least resistance thereby creating uneven flow. The flow distortions and channeling decrease resolution. Where there are many small anomalies, band widening is observed. Where the anomalies are large, band tilting occurs. Sharp bands which are tilted are also observed as broadened peaks during elution. Extraordinary efforts have gone into the production of column packings of spherical particles of uniform diameter to minimize microanomalous flow. The vastly improved resolution obtained with homogeneous, uniform, particle-sized beads demonstrates the key importance of micro-flow control and minimization of channeling. However, homogenous particles do not positively prevent anomalous flow. Even with homogenous particles, the packing may be uneven with local particle compression, or clogging due to the information of precipitates in the packing may occur. Both conditions produce anomalous flow.

Resolution is also lost during flow through tubing into the column (laminar mixing), during radial flow expansion as the fluid flows from the small bore line leading into the column to the wide bore column, during the decrease in cross-sectional area at the bottom of the column, and by laminar mixing during flow to and in the optical flow cell and the intervening tubing.

Arranging a constant column path length was also difficult. The fluid flowing through the chromatographic system may be considered as being composed of many small fluid elements. In free fluid flow these may be kept in order by centrifugal force acting on a density gradient. However, the solutes in these fluid elements are retarded to different degrees by flow through the separative column packings, and if the path length through the packing is different for different solute elements, considerable loss of resolution occurs. If there is a free space at the ends of the columns, considerable mixing occurs in the absence of a gradient combined with a centrifugal field.

If there is no free space at the ends of the columns and the columns merely constrict to a small diameter at each end, then fluid flowing along the edge of the column will flow through a longer path than does fluid flowing along the center axis of the column, resulting in loss of resolution.

Finally, in conventional chromatography careful attention must be paid to eliminating air bubbles and preventing their formation. In some instances degassing of eluting solutions is required.

These were just some of the problems encountered by prior chromatographs. These, and other problems have been addressed by the centrifugal fast chromatograph of the present invention.

SUMMARY OF THE INVENTION

It is an object of the present invention to provide means for performing ion exchange, gel filtration, affinity chromatography, and chromatographic separations of any sort rapidly, in multiple parallel arrangement, efficiently, and relatively inexpensively.

The above and other objects are achieved by the centrifugal fast chromatograph (CFC) of the present invention. The CFC automatically performs, monitors, and compares multiple sample elutions, and regenerates the chromatograph columns. The invention also includes a method of simultaneously conducting gradient elution of a plurality of samples. The CFC includes a chromatograph rotor, and a rotor drive. A plurality of chromatographic columns are equiangularly mounted on the chromatograph rotor and each chromatographic column has an optical flow cell with transparent windows. A sample holding transfer disk is located at the center of the chromatographic rotor. The transfer disk has a plurality of sample wells equiangularly disposed around its periphery. Each sample well corresponds to a respective chromatographic column. Stream apportioning blades are equiangularly disposed on the inner edge of distributor rings of the chromatograph rotor and direct solution from sample wells into the chromatographic columns. The stream apportioning blades also apportion the eluting gradient into the chromatographic columns. Two fluid carrying lines extend from the region of the transfer disk to each chromatographic column. Both have valves to direct fluid to an exit drain. One line is connected to the inner end of the chromatographic column and the other line is connected to the outer end. A light source is mounted on one side of the chromatograph rotor near the periphery and is oriented to shine a light beam through the optical flow cells. A photodetector is mounted above or below the chromatograph rotor opposite the light source to detect light shone through the optical flow cells. A gradient maker is in fluid communication with the chromatographic columns through a distributor ring containing stream apportioning blades which distributes one eluting gradient into all chromatographic columns simultaneously through individual column feed lines. A microprocessor type computer coordinates the operation of the CFC. The microprocessor controls the gradient maker and the rotor drive. It controls the chromatographic process, monitors the chromatographic process and provides real time CRT displays of all chromatographic columns. It also controls an automatic pipetter used to load samples into the transfer disk.

The CFC of the present invention includes a microprocessor which both controls and monitors the separations. A cathode ray tube (CRT) displays the chromatographic separations in real time, while the gradient maker produces the gradient from solutions and controls column regeneration. At the start of an analysis the samples are loaded on the transfer disk in a disk loader. The transfer disk is loaded into the chromatograph rotor at the start of a run, and the rotor is accelerated by the rotor drive under control of the microprocessor. The samples are transferred by centrifugal force from the transfer disk, between respective matching stream apportioning blades, and into their respective column feed lines. Since the transfer disk and the apportioning blades attached to the distributor ring all rotate together, each sample flows uniquely between one matching pair of blades and into one column. The eluting gradient then flows against the same blades, and is apportioned to follow the samples into the column feed lines. Effluent from the rotor may be either led to a drain or collected in a corotating fraction collection ring. Absorbance of the effluent stream is measured by the light source and the photodetector which provides the signal to the microprocessor. The rotor position during rotation is determined using a synchronization signal pickup. Two distributor rings with apportioning blades, one directly above the other, are used. One distributes the eluting gradient during analysis, and the other distributes the regeneration and equilibration solution. An inwardly-projecting lip between the two rings prevents crossflow between the rings.

Operation of the centrifugal fast chromatograph of the present invention provides the required hydrostatic pressure for column packing, chromatographic separation, column regeneration, and sample loading using centrifugal force. Rotation apportions one liquid stream into multiple columns and also provides chopping of the single sensing beam or beams required to achieve reproducible absorbance measurements. The centrifugal fast chromatograph has traps to prevent any column from running dry at rest or during rotation, and valving to control the direction of flow through the columns during analysis and column regeneration. Two types of traps are integral to the design. The first type prevents the columns from draining dry at rest. It includes upwardly-sloping center and edge lines which connect the inner and outer ends of the columns through valves to the central distributor rings. The second type functions during rotation and includes the column and the edge line connecting the column inward to the valve. If liquid feed is stopped during rotation, liquid will drain only up to the open valve and the column will not run dry. If flow is restarted during rotation, air in the feed line will be displaced rapidly by centrifugally forced liquid; the air will move centripitally.

Separated fractions may be collected at intervals and the hydrostatic pressure on the columns may be changed by either changing the rotational speed or the length of the fluid column inward of the separation column. Density gradient elution in the centrifugal field positively stabilizes flow through the system and keeps sample and separated zones from tilting or being widened by anomalous flow. A microprocessor including a liquid gradient generator used with the centrifugal fast chromatograph controls the entire analytical procedure. The centrifugal fast chromatograph may include means for introducing the entire elution gradient into the rotor at one time by enlarging the chambers in the distributor ring, and then for allowing it to flow through the separations columns without additional fluid introduction. Additional optional means for introducing samples and elution gradients into each column unit separately and individually during rotation may be included. Further optional means for driving the rotor using a printed motor incorporated into the rotor itself may be used. A printed motor has its electrical lines and windings "printed" onto plastic-coated metal which may be integral with the rotor. Printed motors can withstand the forces created in stronger centrifugal fields. The direction of liquid flow during elution may be either centrifugal (referred to as System A) or centripetal (referred to as System B). The preferred direction is centrifugal.

Thus, the centrifugal fast chromatograph, in a single apparatus, includes means for moving premeasured samples from a transfer disk into each of several columns aligned with the sample chambers of the transfer disk, means for apportioning one unpressurized gradient stream equally into all columns, and means for providing the hydrostatic pressure required to achieve the separations using centrifugal force. Means for measuring the light absorption of the effluent stream from all columns during rotation and means for collecting fractions from all columns (or for rejecting the effluent stream) are also provided. The present invention also includes means for regenerating all of the columns and, if necessary, monitoring regeneration. Means for positively keeping all zones and boundaries essentially perpendicular to the direction of radial flow and for positively preventing channelling and anomalous flow during gradient elution, means for preventing the columns from running dry either during rotation or at rest, and means for controlling flow so that all parts of a sample or separated zone travel through exactly the same distance in the separation medium during flow between sample application and detection are also included. The centrifugal fast chromatograph also has means for insuring that no air bubbles are retained in the analytical stream, means for collecting samples at predetermined intervals or for rejecting to waste portions of the stream which are of no interest, and means for packing or repacking columns in position.

Flow during elution may be either centrifugal (radially outward), or centripetal (radially inward), with flow in the opposite directions during regeneration. Most of the design descriptions discussed below concern a rotor system (System A) with outboard elution flow, and center flowing column regeneration.

The types of analysis which may be performed on the centrifugal fast chromatograph include but are not limited to the analysis of human plasma proteins, nucleotides and their derivatives, amino acids and their derivatives, urinary metabolites, therapeutic drug monitoring, monitoring for drugs of abuse, and the analysis of the proteins of wheat and other seeds.

Various additional advantages and features of novelty which characterize the invention are further pointed out in the claims that follow. However, for a better understanding of the invention and its advantages, reference should be made to the accompanying drawings and descriptive matter which illustrate and describe preferred embodiments of the invention.

BRIEF DESCRIPTION OF THE DRAWINGS

FIGS. 4A-J illustrate the operational steps of the chromatography rotor.

FIGS. 6A-D illustrate how gradients are used to control flow through long path flow cells.

DETAILED DESCRIPTION OF PREFERRED EMBODIMENTS

Figure 1:
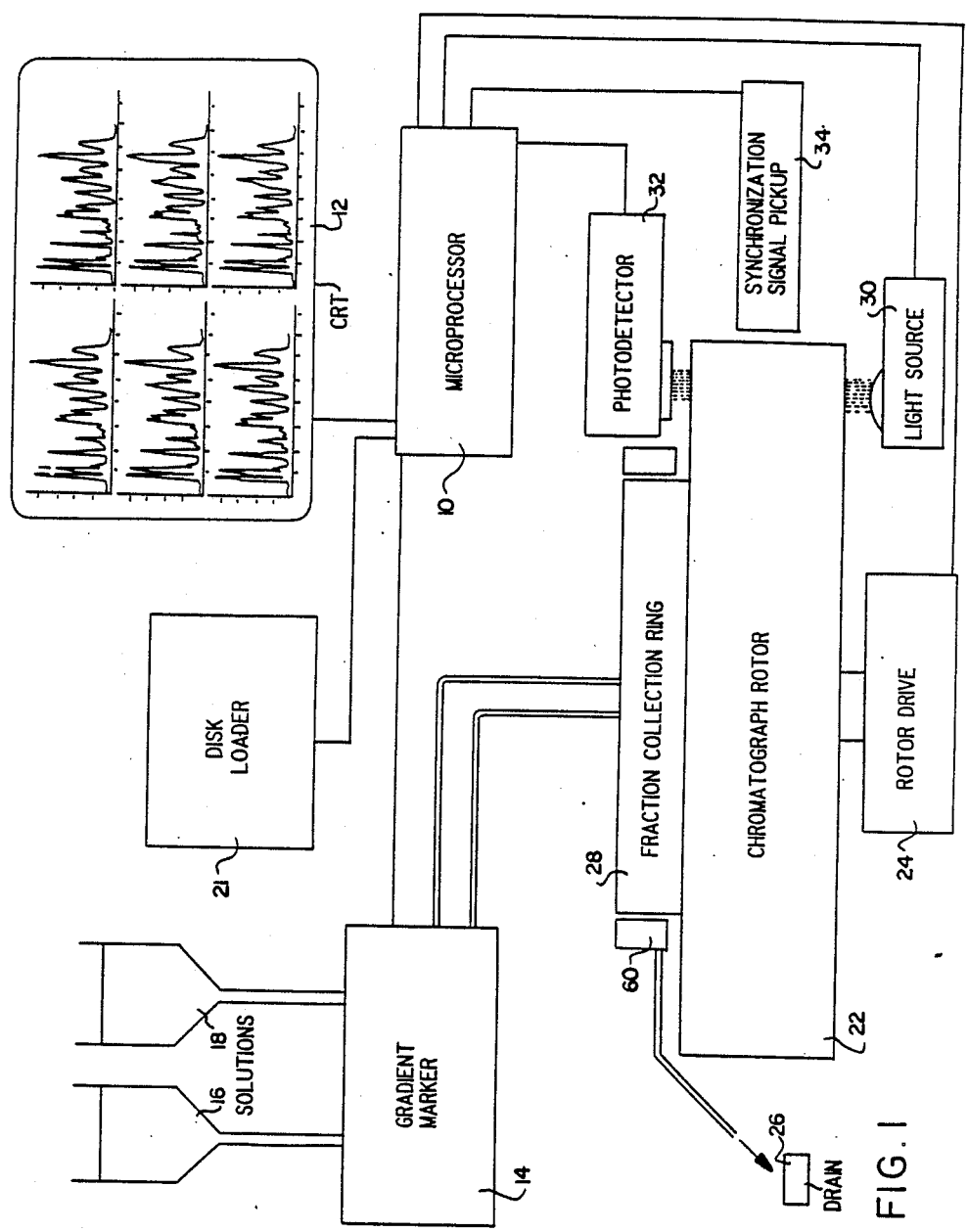
FIG. 1 is a schematic diagram of a centrifugally driven gradient elution chromatographic system according to the present invention.

The central fast chromatograph of the present invention is a centrifugally driven gradient elution chromatographic system. This system is shown diagramatically in FIG. 1. A microprocessor 10 both controls and monitors the separations. Cathode ray tube (CRT) 12 displays the chromatographic separations in real time, while gradient maker 14 produces the gradient from solutions 16 and 18 and controls column regeneration. At the start of an analysis the samples are loaded on a transfer disk 20 (shown in FIG. 2) in disk loader 21 which is an automatic pipetter known in the art. Transfer disk 20 is loaded into chromatograph rotor 22 at the start of a run, and the rotor is accelerated by drive 24 under control of microprocessor 10. Effluent from the rotor 22 may be either led to drain 26 or collected in corotating fraction collection ring 28. Absorbance of light by the effluent stream from light source 30 is measured using photodetector 32 which provides the signal to microprocessor 10. The rotor position during rotation is determined using synchronization signal pickup 34.

Figure 2:
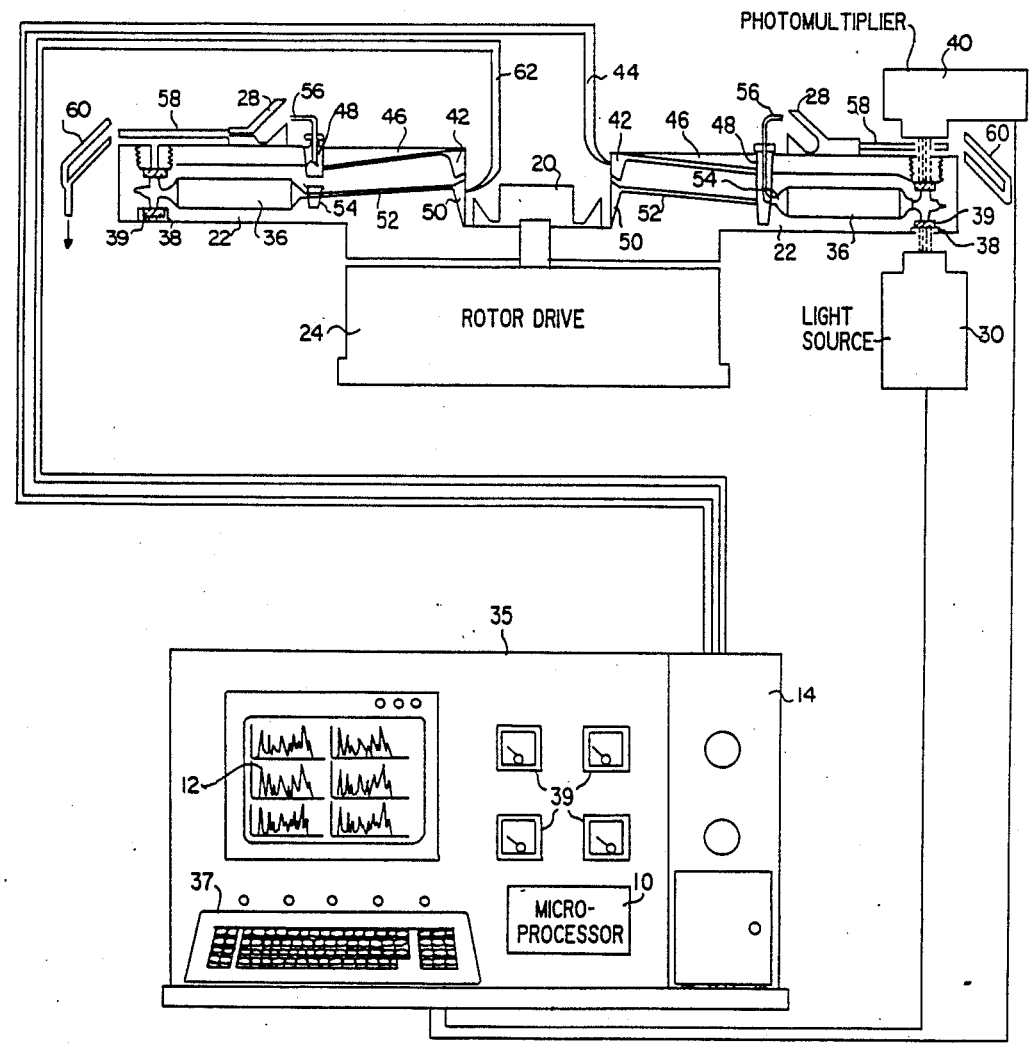
FIG. 2 is a side view of a centrifugally driven gradient elution chromatographic system according to the present invention.

FIG. 2 illustrates a side view of the system. A control center includes a control panel 35, microprocessor 10, CRT display panel 12, keyboard 37, speed and temperature indicators 39, and gradient marker 14. Centrifugal chromatograph rotor 22 is driven by rotor drive 24 which is controlled by the control panel of the control center. Chromatographic columns 36 are mounted for rotation on centrifugal chromatograph rotor 22. The sample-holding transfer disc 20 is mounted in the center of rotor 22. Optical flow cells 38 having transparent windows 39 are mounted on centrifugal chromatograph rotor 22. Light source 30 is mounted opposite photodetector 32, which may be photomultiplier 40, to measure absorbance of the effluent stream. Upper or edge line distributor ring 42 for edge line introduction of the regenerating solution is disposed at the end of solution feed line 44, which runs from gradient maker 14 on the control center 35. Edge lines 46 are fluid carrying feed lines having an antiregurgitation slope disposed between upper distributor rings 42 and edge line valves 48. Lower or center line distributor ring 50 for center line introduction of the regenerating solution is disposed at the end of solution feed line 62, which runs from gradient maker 14 on the control panel 35. Center lines 52 are fluid carrying feed lines having an antiregurgitation slope and are mounted between the center end of chromatographic columns 36 and distributor rings 50. A center line valve 54 (FIG. 3) is disposed on each center line 52 at the center end of chromatographic columns 36. An edge line valve 48 is mounted on one end of an edge line drain 56. Drains and fraction collecting ring 28 is mounted on the other end of edge line drain 56 and includes collecting tubes and collecting ports 58 leading to stationary drain collecting ring 60. Stationary drain collecting ring 60 is mounted on the outside of rotor 22 to collect fluid drained from the rotor 22. Feed line 62 runs from gradient maker 14 to center line distributor ring 50 which is used to elute chromatographic column 36.

Figure 3:
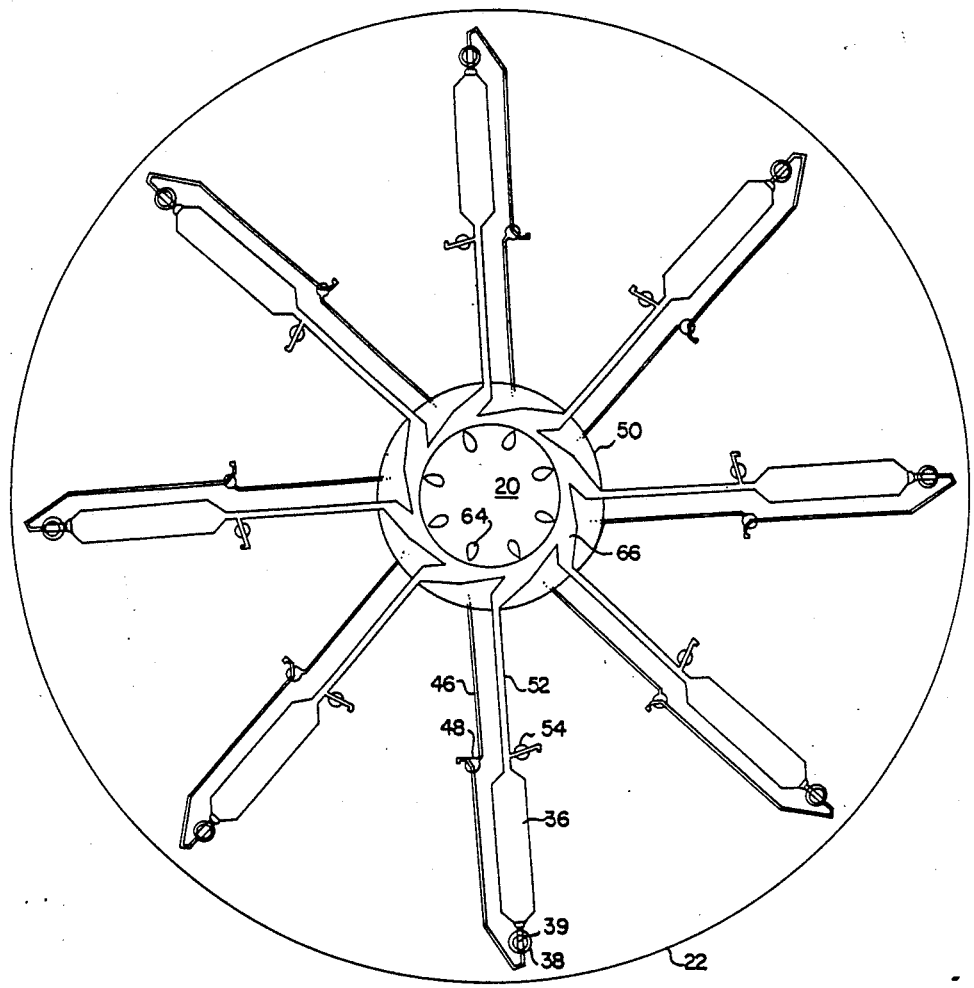
FIG. 3 is a top view schematic diagram of the chromatograph rotor of the centrifugally driven gradient elution chromatgraphic system.

A horizontal section looking down through the System A (centrifugally driven gradient elution) chromatograph rotor is shown in FIG. 3. Chromatograph rotor 22 includes a sample holding transfer disk 20 in which a plurality of sample wells 64 are placed. Sample wells 64 are placed around the outer edge of transfer disk 20 and correspond to respective chromatographic columns 36. Chromatographic columns 36 are connected to the periphery of transfer disk 20 by center lines 52. Stream apportioning blades 66 in center line distributor ring 50 guide the fluid sample between transfer disk 20 and center lines 52. Center line valves 54 are disposed on center lines 52 to divert material to waste during reverse optical flow during column regeneration. Flow cells 38 having transparent windows 39 are disposed on the outer end of chromatographic columns 36 adjacent the connection to edge lines 46. Edge line valves 48 are disposed on edge lines 46 to divert material to waste during elution. Two coaxial stream segmentation devices or distributor rings, upper distributor ring 42 (not shown in FIG. 3) which feeds the edge lines 46 and lower distributor ring 50 which feeds the center lines 52 are used to apportion the stream into multiple columns.

The chromatographic system of the present invention has superior flow characteristics which result in higher resolution. Outward flow during elution (System A), which is preferred requires that the sample be placed at the center end of the chromatographic columns 36, that the optical flow cells 38 or other detector be at the outboard end of the columns 36 and that elution be done with a gradient of decreasing physical density. It also requires that the liquid in the columns 36 at the start be denser than the sample or the starting (heavy) end of the elution gradient. The implications of these special requirements are discussed below.

Figure 5:
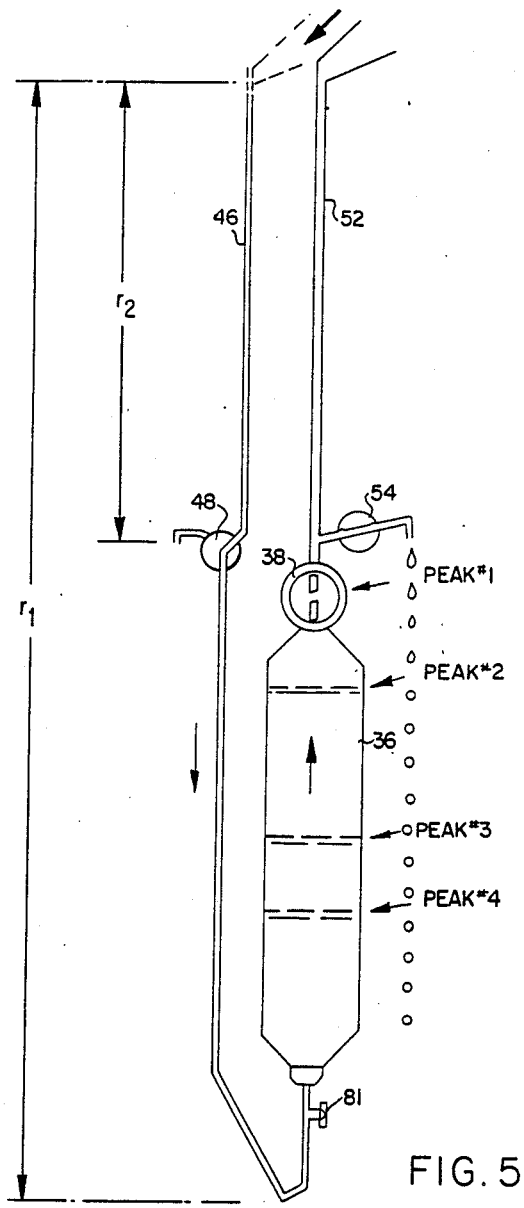
FIG. 5 illustrates inward elution flow in the chromatography rotor.

When center elution flow is used (System B), the fluid in the column at the start is less dense than either the sample or the starting end of the elution solution introduced through the edge line. The elution fluid exits through center line valves 54 on center lines 52, and the elution gradient increases in physical density from start to finish. The sample is applied to the bottom of the columns 36, through the edge lines 46, exits through center line valves 54 on center lines 52, and the optical flow cells 38 are at the top (center end) of the columns 36 as shown in FIG. 5. It is feasible to construct a system that will work either way, and has flow cells at both the tops and bottoms of the columns 36.

The sequence of events during column packing, column regeneration and/or equilibration, and analysis are shown diagramatically in FIG. 4, where the same column is presented in a series of steps involving column packing, regeneration, and analysis. The valves 48 and 54 may be set to allow change in direction of flow. Specifically, during column packing, the suspension being packed flows through the lower stream-segmentation device (distributor ring 50) and into the center lines 52, past the closed center line valves 54, and into the columns 36. Liquid flowing out of the columns 36 past the lower frit flows through the optical cells 38 flow, and to the open edge line valves to drain. When column packing is complete, a small plug may be introduced into the center lines 52, and moved into position by centrifugal force. This prevents packing material from moving and resettling when the rotor 22 is at rest. Sloping of the center and edge lines 52 and 46, respectively is used to prevent fluid from flowing out of the columns 36, flow cells 38, and outer loop when the rotor 22 is at rest.

Figures 4G, 4H, 4I, 4J:
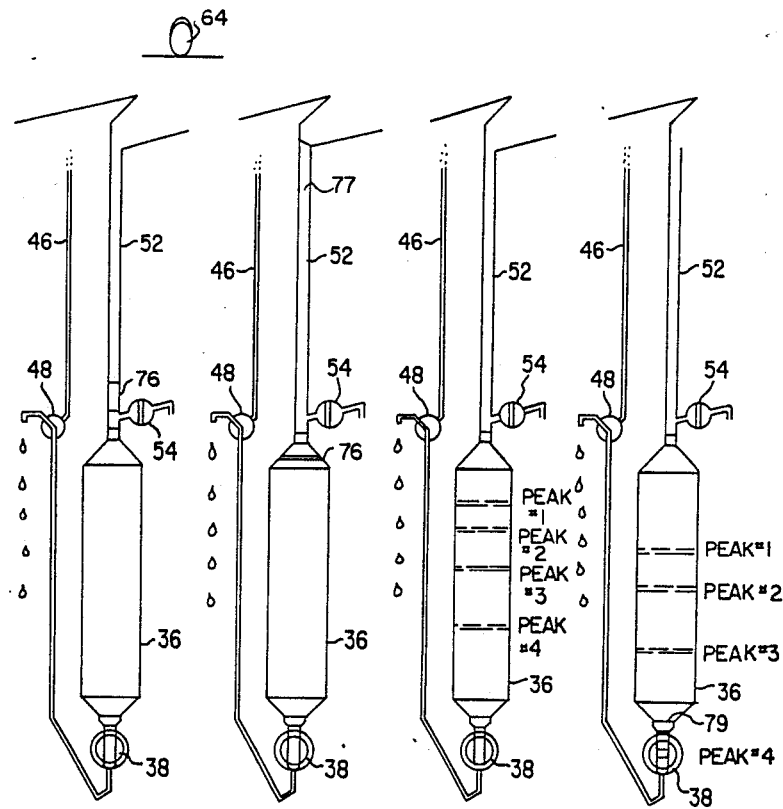

In FIG. 4A a suspension of inert particles 70 is introduced into chromatographic column 36 through center line 52. Both edge line valve 48 and center line valve 54 are set for outward flow, i.e., valve 48 is open and valve 54 is closed. The inert particles 70 pack the lower cone of chromatographic column 36. The active packing 80 which produces the chromatographic separation is then introduced and, in FIG. 4B, chromatographic column 36 has been partially packed due to centrifugal force. In FIG. 4C, all of the active packing 80 is in place, and the upper cone of chromatographic column 36 has been partially packed with inert material 70. In FIG. 4D, chromatographic column 36 has been fully packed and an upper porous plug 72 has been set in place in center line 52 above the chromatographic column 36. In FIG. 4E, edge line valve 48 and center line valve 54 have been set for inward flow i.e., valve 48 is closed and valve 54 is open. During rotation, a washing or regeneration or equilibration liquid 74 is introduced into edge line 46 through upper distributor ring 42 thereby causing column regeneration or equilibration. Liquid density is controlled so that the a liquid whose density is greater than that of the dense end of the elution gradient is left in place in the column 36. A sample 76 is placed in transfer disk 20 adjacent the center line 52 in FIG. 4F while the rotor is stationary. The sample is less dense than the liquid in chromatographic column 36. The edge line valve 48 and center line valve 54 are, once again, set for outward flow i.e., valve 48 is open and valve 54 is closed through chromatographic column 36. In FIG. 4G, the rotor 22 is accelerated and the sample 76 is transferred centrifugally into the rotor 22 and then into center line 52. During continued rotation, an eluting gradient 77 is introduced to the rotor center line 52 as shown in FIG. 4H. Gradient elution of chromatographic column 36 has begun although no separation of the sample 76 occurs in the inert particles 70 in the upper cone of chromatographic column 36. In FIG. 4I, constituents 1, 2, 3, and 4 of the sample have separated in chromatographic column 36. In FIG. 4J, peaks or bands 1, 2, 3, and 4 representing each respective constituent of the sample are eluted sequentially through the cuvet 79 outboard of chromatographic column 36. The peaks move through the cuvet 79 without backmixing. On completion of the analysis illustrated in FIG. 4, column regeneration by back flow occurs and a solution having a density greater than the dense end of the elution gradient is left in place. The analysis may be repeated by beginning with the step illustrated in FIG. 4F.

When the flow is backward through the column 36 during column regeneration and equilibration (hereinafter referred to as System A), liquid flows in through the upper stream-segmentation device (distribution ring 42), out through the edge lines 46, past the closed edge line valves 48, to the centrifugal (outer) end of the column 36, and inwardly through the optical flow cells 38 and column 36, and out through the open center line valves 54 to drain (or collection) 60.

The location of the optical flow cells 38 when elution flow is in an inward or centripetal radial direction during analysis (hereinafter referred to as System B) is shown in FIG. 5, with the optical flow cells 38 located centripetal to (above) the column 36 on center lines 52. In system B, the eluting solution flows through edge line 46 to chromatographic column 36. The pressure head during elution is proportional to the distance D to center line valve 54.

System B has an inherent problem with density reversal in the edge lines 46. At the start of an analysis the least-dense fluid used fills the system. The sample is adjusted to be slightly denser, and will mix rapidly with fluid in the edge lines 46 as it is introduced. Once the sample has passed the hairpin loop at the edge, and begins inward flow, density-gradient stabilization begins to be effective. As the gradient flows into the rotor 22 during analysis, constant backmixing occurs in the edge lines 46 followed by stable flow in the columns 36, flow cells 38, and center lines 52. A solution to the problem of backmixing during sample introduction is to inject the samples individually through a self-sealing rubber port 81 at the centrifugal end of the columns 36 with the rotor 22 at rest. This solves the problem, but makes the system less desirable from the automation viewpoint.

During sample loading followed by introduction of the gradient, flow and valve settings are as shown in FIG. 5. Column regeneration involves flow of solution in through center line 52, and drainage out through the exit port of valve 48, i.e., the flow and valve settings are the same as for column packing.

The CFC has automatic compensation for flow resistance in different columns that maintaines constant flow. In the CFC, the actual pressure head on each column is a function of the length of the liquid column center of the exit line. If one column has slightly less resistance to flow than the other columns, fluid will flow more rapidly, the length of the liquid column will decrease, there will be less driving pressure, and flow through that column will automatically adjust itself to match the others, provided that the liquid gradient is not introduced too rapidly. The upper portion of the column center of the exit line can be expanded to include a large volume of fluid, up to and including the entire gradient. In a centrifugal field large density gradients are stable. Air bubbles will not impede flow as air bubbles are forced inwardly by the centrifugal field.

During elution with either system A and System B, the gradient used is a bifunctional gradient, varying first in density or specific gravity to control flow and maintain fluid segments in their proper sequence, and second in eluting power, to sequentially elute components of the mixture being analyzed from the column.

With System A, the liquid regeneration or equilibrium 74 in the rotor, the sample 76, and the elution gradient 77 must be arranged to be in order of decreasing density. For much protein and other work involving reverse phase chromatography, the gradient 77 is one of increasing acetonitrile concentration. Acetonitrile has a density or specific gravity of 0.785 g/ml; hence a gradient from water or a customary buffer solution will grade from a density of approximately 1.000 g/ml to 0.785 g/ml. The specific gravity will decrease as required for System A. If sucrose or other inert gradient material is added to the equilibration solution 74, optionally to the sample 76, and to the denser of the solutions used to make the gradient 77, a steeper density gradient may be obtained.

When the gradient 77 normally used is one of increasing salt concentration and is therefore of increasing density, an inert density-increasing material must be added to the equilibration solution, in lesser amount to the sample 76, and must be in decreasing concentration in the gradient 77 to yield a gradient of decreasing physical density, but of increasing elution power. This is one disadvantage of System A when used with columns and elution procedures requiring very concentrated salt solutions. With System B, which requires a gradient 22 of increasing density, gradients which are natively of increasing density may be used directly.

The disadvantage of System B is sample-zone smearing during flow through the edge lines 46. This may be minimized by having very small bore edge lines 46. The smearing may be of little effect in instances where the sample 76 is strongly absorbed in a small volume of column packing material 80 at the start of flow through the columns 36, thereby reconcentrating the sample 76 at the outset into a small volume. Injection of the sample 76 at the rotor edge initially also solves this problem but introduces operational disadvantages.

An advantage to System B is that flow is counter to centrifugal force. Therefore flow is tending to resuspend the column packing, while centrifugal force is tending to pack it down. This sets a limit to the flow rate without positive positioning of an upper frit. With System A, flow and centrifugal force are in the same direction, hence flow and centrifugal force will combine to pack down the column material 80 more. This is a disadvantage with column packings 80 which are deformable, and can be overcompressed causing flow reduction.

With the systems described here, which use density gradients, extraordinary control of flow is achieved by centrifugal force. This is illustrated by considering the effect of a 0.001 increment in density in a field of 5,000 g. This produces an effect equivalent to a difference in density of 5 grams/ml.

The stabilizing effect of the gradient will also be seen in the optical flow cells 38. To increase the sensitivity of detection, a long optical path is desired. This is often attained by using a cylindrical micro-bore flow cell as shown in FIG. 6A in which liquid from chromatographic column 36 flows into optical micro flow cell 38. The liquid is illuminated by light from light source 30 which passes through windows 39. In static systems, this often presents cleaning problems, and becomes useless with the presence of small air bubbles. In addition, resolution is lost by laminar mixing. These problems are not a factor with the centifugal fast chromatograph. If a long-path flow cell 38 with a reasonable optical cross-section is arranged as shown in FIG. 6B, then, when no gradient is present, laminar mixing will greatly increase peak width and decrease resolution. However, with centrifugal gradient stabilization, no mixing occurs as shown in FIG. 6C. The zone or peak 100 is stabilized as it passes through the flow cell 38. The peak 100 flows through the flow cell 38 without an appreciable volume change, and the resolution obtained in the column 36 is not degraded during detection. FIG. 6D is an end view of the flow cell 38 of FIGS. 6B and 6C, illustrating the very narrow one dimensional cross section.

Figure 7A:
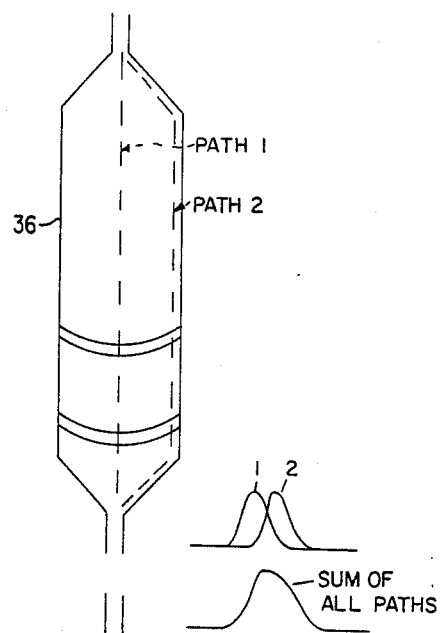
FIGS. 7A-D illustrate how the path length is controlled in the chromatographic column through column packing.
Figure 7B:
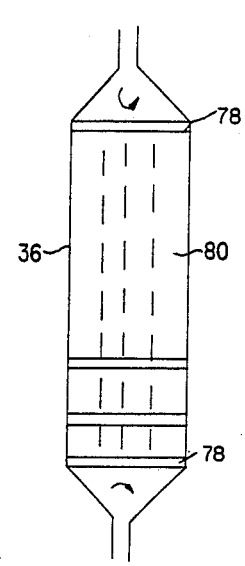

The CFC provides constant column path length. This overcomes resolution loss as illustrated in FIGS. 7A–D. FIGS. 7A–D shows how the path length is controlled as the eluting gradient 77 moves through the column packing 80, and how mixing in a free space at the ends of the column 36 is overcome by the centrifugal field. In FIG. 7A, a fully packed column eluted at rest is shown. Different fluid elements traverse different distances. Peaks from paths 1 and 2 are graphically shown along with resolution loss as all paths are summed. In FIG. 7B, the column is also eluted at rest. Mixing occurs in the free space above the upper frit and the free space below lower frit 78. Thus, as shown, the separation distance for all paths is identical, but resolution is lost in the free spaces at the ends.

Figure 7C:
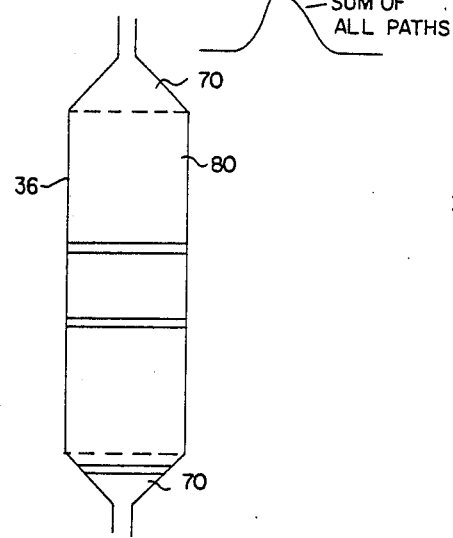

If the cones at the end of the column 36 are filled with inert material 70 which does not contribute to the separation, then in a centrifugal field the gradient 77 and centrifugal force will stabilize zones within the cones so that they widen evenly in the cones, and little resolution is lost. All fluid elements having the same density then pass through identical distances in separative packing 80 as shown in FIG. 7C. Retarded solute zones, shown as dark bands, are therefore kept sharp and do not tilt.

Figure 7D:
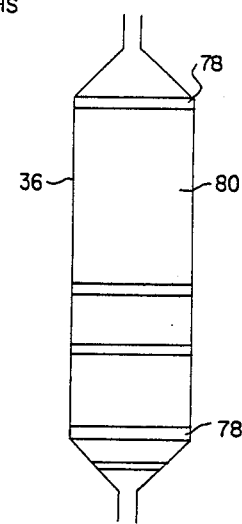

If strong frits are available which will withstand the centrifugal force, then an open-cone construction can be used at the bottom of the column as shown in FIG. 7D. The frit shown at the top may be a plug held in place by centrifugal force. Flow is controlled by the gradient in the centrifugal force field in the cones and in the body of the column, and separated zones are kept perpendicular to the direction of centrifugal force as shown, and high resolution is achieved.

With the CFC there are no "wall effects" such as occur when particles are sedimented in a centrifugal field. Therefore, the separation chamber (i.e., the column 36) can have almost any configuration including that of a cube, a cylinder, a sector, or an inverted sector.

In the CFC, gradient overloading which may cause mixing and inversions will rarely occur except at the original sample zone or early in the course of elution. Hence the greatest density slope must occur immediately under the sample 76 initially, and later in those parts of the elution gradient 77 containing the most sample mass. The "turnover effect" which is well known in density gradient centrifugation and is due to differential diffusion of the sample solution 76 down into the gradient 77, and the diffusion of the gradient solution 77 back up into the sample 76 will not be a problem in the chromatograph rotor because of the short time between sample introduction and initiation of separation which minimizes diffusion, and because the differences in molecular mass between the gradient 77 solution and the sample 76 are not as large as in the zonal centrifuge separation of subcellular particulates.

Air bubbles are not a problem in centrifugal chromatography where the centrifugal fields are sufficiently large to move any air bubbles completely out of the column 36 and flow lines 46 and 52. Thus, even in very small bore lines filled with air, samples will flow past the air and quickly displace it centripetally. Also, because gas solubility is a function of pressure, should any air bubbles (or other gas bubbles) occur, they will tend to redissolve rapidly given the pressures existing in the rotor during rotation.

The design of the system prevents the columns 36 from ever running dry. The exit lines 46 and 52 are all center of the columns, and are tilted up at some point along their length. Providing the exit lines 46 and 52 inboard of the columns 36 prevents their running dry during rotation. Traps are thus provided in the lines as an integral part of their design.

The gradient maker 36 may be of a positive type using differentially driven pumps to mix two or more liquids to produce a liquid gradient, or a passive type in which two containers having complementary geometries are drained by gravity through a mixer to form a gradient. These are well known. One or more liquids are also required for column regeneration, and these are introduced by reverse flow through the columns after adjusting either manually or automatically the feed line and drain line valves 48 and 54. The gradient 77 or the regeneration solutions flow into the centrifugal chromatograph during rotation.

The methods for signal acquisition, data processing, signal averaging, data display, and the analysis of chromatographic data are well known.

In the designs described, the driving forces are generated by the difference in radius of the center (centripetal) fluid column ($r1$), and the radius of the drain exit ($r2$), as shown in FIG. 5. Centrifugal force is directly proportional to radius. Hence, the pressure generated by this difference in radius is equal to the average $r=(r1+r2)/2$ multiplied by the centrifugal force, multiplied by the liquid density, and multiplied by the column length. If the pressurizing column extends from 4 cm to 20 cm ($r1$ and $r2$), the centrifugal force is calculated at 12 cm, and the pressure column is 16 cm long. At 3000 rpm the centrifugal force at 12 cm results in a pressure head of 19,440 $g/cm^2$, or 276.5 psi. At 4000 rpm the centrifugal force at 12 cm results in a pressure at the bottom of the pressure column of 33,400 $gm/cm^2$, or 489.28 psi.

A variety of methods for operating the two valves attached to each column are possible. Several are discussed below. In the illustrations provided thus far, the two valves are operated separately and manually. It is evident that since the valves are always operated simultaneously that each pair may be interconnected, and that all valves may be operated by one mechanism. The valves may be pressure operated, centrifugally operated, electrically operated, or mechanically operated.

Figure 8A:
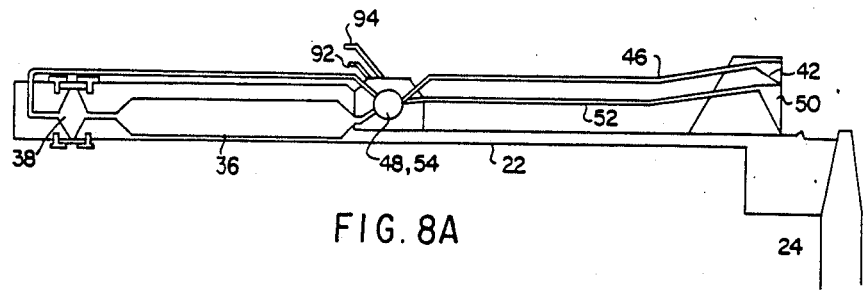
FIGS. 8A-D illustrate a piston operated valve system used with the centrifugally driven gradient elution chromatographic system of the present invention.
Figure 8B:
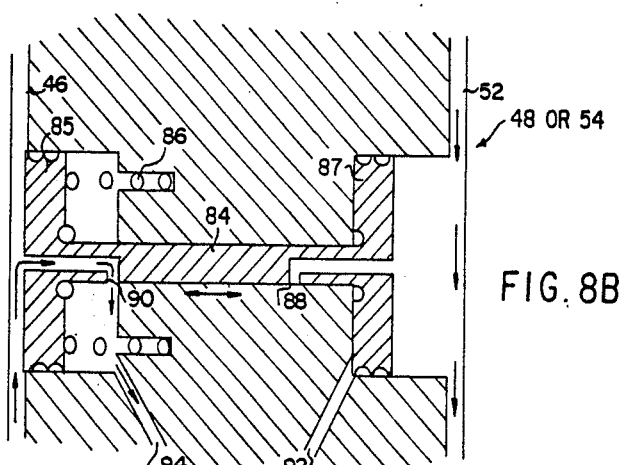
Figure 8C:
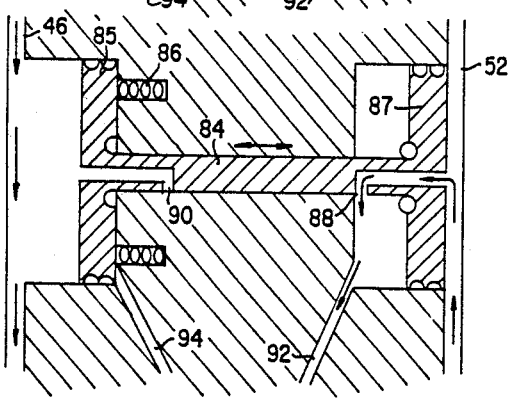
Figure 8D:
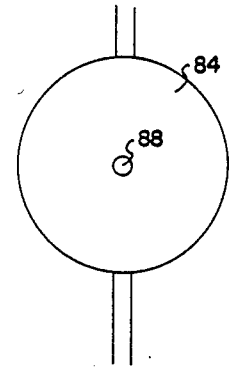

Pressure operated valves are illustrated in FIGS. 8A–C. When one of the lines 46 or 52 attached to the column 36 is full of liquid, the other 46 or 52 is empty out to the exit valve 48 or 54. Hence there is considerable hydrostatic pressure in one line. If liquid suddenly runs through one set of lines during rotation, pressure sufficient to close the valve attached to that line is created. By continuing flow into the line with the closed valve, the valve is kept closed. When liquid flow in ceases, the liquid level will gradually drop to equal that of the other line (i.e., the exit valve level), and sudden liquid introduction into the opposite line will reverse the valve setting. Operating details are shown in FIG. 8 using a piston operated valve. FIG. 8A is a side sectional view of the chromatograph rotor 22 showing the position of piston operated edge line valves 48. In FIG. 8B, piston operated valve 48 or 54 (used for both center lines 52 and edge lines 46) is in its rest position preparatory to column elution. Piston 84 has two head portions 85 and 87 and a spring 86 biasing piston 84 to the left. Piston has two openings 88 and 90 through its center to permit passage of liquid. First opening 88 provides a fluid passageway from center line 52 to drain 92 and second opening 90 provides a fluid passageway from edge line 46 to drain 94. When piston 84 is driven to the left, the edge line-drain connection 90 is open and the center line-drain connection 88 is closed. In FIG. 8C valve is in position for column regeneration. Edge line 46 is filled during rotation and exerts a pressure on the left of piston 84 sufficient to drive piston 84 to the right, thereby closing edge line to the drain and opening center line 46 to drain 94. FIG. 8D is an end view of piston showing the opening 88 in the center.

In centrifugally operated valves, centrifugal force either alone or in combination with hydraulic pressure is used to operate the valves. Spring loaded valves are well known, and can be arranged so that they are in one position at rest (due to spring loading), and in the alternate position in a centrifugal field where centrifugal force opposes the spring. Spring tension can be set so that position change occurs at relatively high speed, making it possible to regenerate columns at one speed, and elute at a second. It is also feasible to combine centrifugal operation with hydrostatic pressure-operated valves so that once the positional change occurs, hydrostatic force maintaines that position.

In electrically operated valves an electric drive system is used in the chromatograph rotor to change all valve positions at once.

In mechanically operated valves, the valves are arranged so that they are operated by mechanical movement. For example, the valves may be arranged so that the members of a pair are one above the other, on shafts that extend above and below the rotor. With a vertically-moving non-rotating ring all of the extensions may be simultaneously pushed down from above, or with a similar ring placed below the rotor, all may be pushed up.

Detection of valve operation failure may be important in routine long term operation. If the edge and center line drains open into separate drain collection rings (not shown), then it is a simple matter to determine that fluid flow exists from one ring, and is absent from the other. If flow occurs from both collector rings, then valve failure has occurred.

The center line can be enlarged, especially at its inboard end, to hold a considerable volume of liquid, in the limiting case, the entire elution gradient volume.

Because the system will not run dry during rotation, there is no lower limit for the rate of feed of elution buffer. However, if the elution feed rate is too high, liquid will flow out of the center line distributor ring. In one modification of the system, this liquid is guided to the center line collecting ring and is detected. The elution flow rate may then be increased until fluid is detected in the center line collecting ring, and then decreased until the rate of elution buffer outflow matches inflow. Similarly, the edge line distributor overflow may be guided to the edge line collecting ring which normally collects no fluid during regeneration, and excess flow during regeneration detected.

For most applications fractions are not collected, and the fraction collector described here is omitted, and the exit lines are led directly to the drain collecting ring. However, when fraction collection is desired, then a fraction collector ring 28 is provided which corotates with the chromatograph rotor of the CFC but can be indexed around to collect separate fractions from each chromatographic column 36. The initial setting of the fraction collector ring 28 is designed so that each exit line drains through the collector ring 28 to the drain ring 60 and to waste. This allows column regeneration, and also allows the initial part of the elution gradient to be discarded.

The fraction collector ring 28 may be designed to receive tubes 58, but it is more optimally designed to hold flattened collection chambers which allow a very much larger number of collection units to be compressed into the limited space of the collector ring 28. Tubes or flattened collection chambers are angled so that they do not spill either at rest or during rotation.

The position of the rotor 22 during rotation is sensed by a small electromagnetic or optical pickup positioned next to the chromatograph rotor 22, and a similar pickup determines the position of the collector ring 28. Using a suitable algorithm the position of the ring relative to the exit lines is determined, and the identity of the collection vessels being used is known.

To advance the collecting ring 28 one unit (one tube or collecting vessel), a variety of mechanical, electrical, or hydraulic mechanisms may be used. The preferred method uses a mechanical brake to apply a small force to the collecting ring 28, retarding it relative to the chromatograph rotor 22. A ratcheted escapement mechanism allows the collector to move only the width of one collecting vessel. The ratchet is then operated using either downward force applied through a ring above the rotor, electrical force, or a retarding force applying pressure to a spring which resets the ratchet when the retarding force is relased. Escapement mechanisms suitable for this purpose are well known.

It is feasible to use a large seal of teflon or other self lubricating material attached to a central bell-shaped chamber to isolate the center of the rotor from the rest of the rotor chamber, and to keep the center at atmospheric pressure while a vacuum is produced in the rotor chamber. This produces an additional driving pressure of one atmosphere across the column in the rotor, and also allows the contents of the collecting vessels to be concentrated by evaporation or lyophilization in a centrifugal field. This is of great advantage when concentration is necessary. Also, the centrifugal force makes the drying process much more efficient, and material does not fly off the evaporation surface due to bumping or boiling.

The column fittings can be arranged so that columns may be prepacked and attached to the chromatograph rotor, or may be changed as necessary.

Numerous characteristics, advantages and embodiments of the invention have been described in detail in the foregoing description with reference to the accompanying drawings. However, the disclosure is illustrative only and the invention is not limited to the precise illustrated embodiments. Various changes and modifications may be effected therein by one skilled in the art without departing from the scope or spirit of the invention.

I claim:

1. A method of simultaneously conducting gradient-elution of a plurality of solutions using a centrifugal fast chromatograph having a valve system for reversing flow through columns while maintaining centrifugally-generated pressure and flow comprising the steps of:
   placing a sample in a transfer disk of a chromatograph rotor;
   placing gradient solutions in a gradient maker;
   transferring a gradient from said gradient maker through gradient feed lines, distributor rings, and feed lines, and into chromatographic columns;
   eluting the samples by the gradient and by rotating said chromatographic columns;
   monitoring the separated solutions with a photodetector and a light source which detect the state of the solutions through an optical flow cell disposed in each said chromatographic column; and
   simultaneously controlling, monitoring and recording all aspects of the chromatographic process for said chromatographic columns.

2. The method as set forth in claim 1 further comprising the step of:
   automatically apportioning the sample into multiple streams using stream apportioning blades on said chromatograph rotor, thereby transferring equal amounts of said sample into said chromatographic columns.

3. The method as set forth in claim 1 further comprising the steps of:
   introducing a suspension of inert particles to pack a lower cone of said chromatographic columns while center and edge line valves are set for outward flow through said chromatographic columns;
   packing said chromatographic columns with active particles by centrifugal force;
   packing an upper cone of said chromatographic columns with inert particles; and
   setting in place an upper porous plug in each said chromatographic column.

4. The method as set forth in claim 3 wherein samples are individually injected through self-sealing rubber ports at the centrifugal end while the rotor is at rest to prevent backmixing.

5. The method as set forth in claim 1 wherein hydrostatic pressure provided by centrifugal force assists packing of said chromatographic columns, loading the sample into said chromatographic columns, separating the samples during elution, and regenerating said chromatographic columns.

6. The method as set forth in claim 1 wherein the density gradient elution in a centrifugal field is conducted so as to stabilize flow of the sample through said chromatographic columns and prevent anomalous flow including band tilting, band widening, and channeling.

7. A method of simultaneously conducting elution of a plurality of sample solutions using a centrifugal chromatograph having a plurality of rotatable chromatographic columns and a valve system for reversing flow through the columns while maintaining centrifugally-generated pressure and flow comprising the steps of:
   selectively placing a sample in flow communication with either end of a chromatographic column;
   selectively placing solutions in flow communication with said chromatographic columns for eluting the sample from said selected end;
   eluting the sample with the gradient by rotating said chromatographic columns to produce separated solutions in the columns.

8. The method of claim 7 further comprising the step of monitoring the separated solutions to detect the state thereof.

9. The method of claim 7 further comprising the step of apportioning the sample into multiple streams for flow communication with each of said chromatographic columns.

10. The method of claim 7 further comprising the step of producing a density gradient in the solution for stabilizing the flow of samples through the chromatographic columns.

11. The method of claim 7 further comprising the step of preventing regurgitation of the sample and the solution from the chromatographic column.

* * * * *